United States Patent [19]

Ohnishi

[11] Patent Number: 4,851,404
[45] Date of Patent: Jul. 25, 1989

[54] METHOD OF TREATING HEMOGLOBINOPATHY

[75] Inventor: S. Tsuyoshi Ohnishi, Philadelphia, Pa.

[73] Assignee: Miles Inc., Elkhart, Ind.

[21] Appl. No.: 691,654

[22] Filed: Jan. 15, 1985

Related U.S. Application Data

[63] Continuation-in-part of Ser. No. 510,593, Jul. 5, 1983, abandoned.

[51] Int. Cl.$^4$ .................. A61K 31/55; A61K 31/495; A61K 31/44; A61K 31/40
[52] U.S. Cl. .................................. 514/211; 514/255; 514/356; 514/428; 514/523; 514/815
[58] Field of Search ............... 514/815, 211, 255, 356, 514/428, 523

[56] References Cited

U.S. PATENT DOCUMENTS 4,383,997  5/1983  Boucher .............................. 424/253

OTHER PUBLICATIONS

"Calcium Blockers", edited by Flaim et al., Urban & Schwarzenberg, Baltimore-Munich 1982, pp. 139, 140, 170-173, 183-187 & 196.
Ann. Soc. Med. Trop. 1969, 49 z, 205-210.
J. Int. Med. Res. (1976) 4, 375-381.
"Development of Therapeutic Agent for Sickle Cell Disease", 1979, North-Holland Pub. Co. AM.-N.Y-OX. pp. 7-11 & 195-202.

*Primary Examiner*—Frederick E. Waddell
*Attorney, Agent, or Firm*—E. P. Gray; M. G. Boguslaski

[57] ABSTRACT

A therapeutic method of treatment of hemoglobinopathy by administration of a drug capable of blocking the $Ca^{+2}$ channel in and out of muscle cells. Drugs known to possess this capability are 1,4-dihydropyridines, $\beta$-phenethylamines, benzothiazepines, ethylenediamines and diaryl alkyl amines. These drugs are known to block the influx of $Ca^{+2}$ into the cardiac muscle and are known to be useful in treatment of such heart muscle conditions as angina. It has now been unexpectedly discovered that such drugs can be used to treat hemoglobinopathy.

10 Claims, No Drawings

METHOD OF TREATING HEMOGLOBINOPATHY

This application is a Continuation-In-Part of co-pending U.S. application Ser. No. 510,593, filed July 5, 1983, now abandoned, the disclosure of which is incorporated herein by reference.

BACKGROUND OF THE INVENTION

1. Field of the Invention

Normal red blood cells have a biconcave shape and are easily deformable. Red blood cells are oxygenated in the lungs and travel through blood vessels to the capillary bed where oxygen delivery to the tissues is carried out. During this oxygenation-deoxygenation cycle, because they are deformable, normal red blood cells are able to pass through capillary channels which are narrower than the red blood cells.

In 1910, abnormal red blood cells in the peripheral blood of a patient with unexplained anemia led to the first description of what is now called "sickle cell anemia" (SCA). It was observed that the deformed cells had thin, elongated, sickle and crescent-shaped forms and lacked normal deformability.

It has now been established that SCA and related diseases, e.g., thalassemia, are types of hemoglobinopathy caused by abnormal hemoglobin due to a genetic disorder of hemoglobin. When normal hemoglobin becomes deoxygenated, the manner in which its four peptide chains are folded becomes different from that of oxyhemoblogin. In SCA and thalassemia, the abnormal hemoglobin polymerizes upon deoxygenation, causing aggregation of the molecules and distortion of the cell into its characteristic sickle shape, having decreased deformability. This decreased deformability can produce pathological manifestations which include painful vaso-occlusive crisis, bone infarct, cellulitis, osteomyelitis, or anemia (splenic infarct).

The majority of red blood cells of SCA patients become sickled when deoxygenated and return to the original unsickled shape when reoxygenated, i.e., sickling is generally reversible. However, there are a certain number of permanently deformed cells in the circulation of such patients (from 2 to 30 percent) which maintain a sickle shape even after prolonged oxygenation. These abnormal cells are called "irreversibly sickled-cells" (ISC) and because of this lack of deformability, these cells are sequestered and destroyed in reticuloendothelial organs such as the spleen and liver. This is considered to be the major cause for the anemic condition of the patients.

2. Description of the Prior Art

Because SCA and thalassemia involve polymerization of abnormal hemoglobin, most investigators have been searching for compounds which can bind with hemoglobin and inhibit polymerization of deoxyhemoglobin. Urea and cyanate have been proposed as antisickling compounds on the basis of results which indicate that these compounds inhibit the formation of deoxyhemoglobin polymer in vitro. Because the concentration of hemoglobin within the red blood cells is about 5 mM, the concentration of a compound which binds to the hemoglobin to inhibit polymerization must be on the same order of concentration or higher. Clinical tests of urea and cyanate have shown that various side effects prohibit the use of those compounds.

*Proc. Natl. Acad. Sci.*, 77, 2955–2959 (1980), describes a new concept of anti-sickling compounds, e.g., cetiedil, which inhibit sickling based upon interaction with red blood cell membranes. *E.J. Pharm.*, 75, 121–125 (1981), describes the use of nonneuroleptic forms of anti-psychotics in anti-sickling therapy. *Proc. Natl. Acad. Sci.*, 72, 4153–4156 (1975) and 73, 3288–3292 (1976) describes the use of sulfhydril reagents in anti-sickling therapy. U.S. Pat. No. 4,137,309 describes normalizing the deformability of sickle-cells by administration of organophosphates. *The Anticalcium and Erythrocyte Membrane Effects of Zinc, and their Potential Value in the Treatment of Sickle Cell Anemia*, Brewer and Kruckeberg, Department of Human Genetics, University of Michigan Medical School, Ann Arbor, Mich. (1979), pages 195–202, proposes treating SCA with zinc sulfate or zinc acetate. Brewer et al set forth various theories as to why the zinc may work. One theory is increase in erythrocyte oxygen affinity. Another is inhibition of polymerization of deoxyhemoglobin, such as indicated for urea and cyanate mentioned supra. Brewer et al also speculate about zinc having some effect on the flux of $Ca^{+2}$ through the membrane of red blood cells. The flux of $Ca^{+2}$ through the membrane of red blood cells is extensively discussed in Rosa et al, "Development of Therapeutic Agents for Sickle Cell Disease", Inserm Symposium No. 9, Institut National de la Sante et de la Recherche Medicale, North-Holland Publishing Company (1979).

On the other hand, Brewer et al at page 196 specifically state that the "decrease in sickle cell pain crisis frequency . . . must be viewed with caution in view of the strong placebo effects possible". In other words, Brewer et al are proposing that zinc may only treat the symptoms, i.e. alleviate the sickle cell pain crisis, rather than treat the sickling phenomenon. In particular, Brewer et al at pages 198–199 point out that disagreement exists as to the role of $Ca^{+2}$ in the formation of sickled blood cells, and it has been observed that ISC's can be induced to form in the absence of $Ca^{+2}$. Also, it is mentioned that the zinc compounds cause a copper deficiency (Brewer et al at page 196).

Obviously, there has been a long felt need for a compound to treat SCA. Because hemoglobinopathy is caused by a genetic defect, SCA patients will have to undergo a therapeutic regimen for extended periods of time. Therefore, the toxicity and other undesirable side effects of such drugs in long-term administration will be critical in the treatment of such patients. Compounds such as urea, cyanates, sulfhydrils and organophosphates suffer the disadvantage of toxic side effects, and zinc causes a copper deficiency.

Neither the articles or the patent discussed above disclose or suggest that drugs capable of blocking the calcium $+2$ channel in and out of muscle cells can be used to treat hemoglobinopathy. Such $Ca^{+2}$ channel blocking drugs have been shown to be safe for long term administration.

Flaim et al, *Calcium Blockers*, Baltimore-Munich, pages 139, 140, 170–173, 183–187, 196 (1982), discuss many of the $Ca^{+2}$ channel blocking drugs of the instant application with particular emphasis on verapamil, nifedipine, and diltiazem. Specifically, Flaim et al at page 140 are concerned with the chronotropic and inotropic effects of these three drugs on the cardiac muscle. The book, *Calcium Channel Blocking Agents in the Treatment of Cardiovascular Disorders*, edited by Stone and Antman, Futura Publishing Co., (1983) is an anthology of earlier published papers discussing the effects and mechanisms of such $Ca^{+2}$ channel blocking drugs on the flux of $Ca^{+2}$ in and out of myocardial cells. From Stone and Antman and from Flaim et al it is quite clear that the $Ca^{+2}$ channel blocking drugs which they discuss are known for treating heart muscle conditions such as angina. Nowhere do either of these references suggest anything to the person skilled in the art and knowledgable about zinc treatment for SCA that "muscle cell" $Ca^{+2}$ blockers would be effective in treating "red blood cell" conditions because the same term "$Ca^{+2}$ blockers" is being used in two different ways. Thus, it is to be understood that the term $Ca^{+2}$ channel blocking drugs, when used in this specification, is intended to mean those drugs which are capable of blocking the influx and efflux of $Ca^{+2}$ through muscle cells.

SUMMARY OF THE INVENTION

The present invention is directed to a therapeutic method for treating hemoglobinopathy. The method involves administering to a patient a therapeutically effective amount of a drug capable of blocking the $Ca^{+2}$ channel in and out of muscle cells to inhibit the formation of irreversible sickle cells.

DETAILED DESCRIPTION OF THE INVENTION

The present invention involves the inhibition of formation of irreversibly sickled-cells in hemoglobinopathy by administration of a $Ca^{+2}$ channel blocking drug. $Ca^{+2}$ channel blocking drugs include 1,4-dihydropyridines, such as nitrendipine, nifedipine, nimodipine, nisoldipine and niludipine. Other $Ca^{+2}$ channel blocking drugs include $\beta$-phenethylamines such as tiapamil and verapamil; benzothiazepines such as diltiazem; ethylenediamines such as bepridil; and diaryl alkyl amines such as lidoflazine, prenylamine, fendiline, terodiline, cinnarizine and flunarizine.

In the present specification, the expression "diluent or carrier" means a pharmaceutically acceptable nontoxic substance that when mixed with the active ingredient or ingredients renders it suitable for administration. Other pharmaceutically acceptable ingredients such as salts in correct quantities to render the composition isotonic, buffers, surfactants, coloring and flavoring agents, and preservatives can be present. Examples of suitable solid and liquid diluents and carriers are the following: water containing buffering agents which can be rendered isotonic by the addition of glucose or salts; nontoxic organic solvents; such as paraffins, vegetable oils; alcohols; glycols; natural ground rock (for example, kaoline, aluminas, talc or chalk); synthetic rock powders (for example, highly dispersed silica or silicates); and sugars.

Oral administration can be effected utilizing solid and liquid dosage unit forms such as powders, tablets, dragees, capsules, granulations, suspensions, solutions, and the like. Where appropriate, dosage unit formulations for oral administration can be microencapsulated to prolong or sustain the release, as for example, by coating or embedding particulate material in polymers, wax, or the like.

Parenteral administration can be effected utilizing liquid dosage unit forms, such as sterile solutions and suspensions intended for subcutaneous, intramuscular or intravenous injection. These are prepared by suspending or dissolving a measured amount of the compound in a nontoxic diluent or carrier suitable for injection, such as an aqueous or oleaginous medium and sterilizing the suspension or solution. Stabilizers, preservatives, and emulsifiers can also be added.

Generally, the parenteral dosage of the $Ca^{+2}$ channel blocking drug in a composition for administration wil be from 0.1 to 10 mg/kg, preferably from 0.1 to 5 mg/kg, of body weight per day, and the oral dosage form will be from 0.1 to 100 mg/kg, preferably 0.5 to 50 mg/kg, of body weight per day.

The procedure used to demonstrate the effectiveness of the $Ca^{+2}$ channel blocking drugs in inhibiting the formation of ISC in a patient having sickle-cell anemia is described below.

Red blood cells from patients with SCA were exposed to repeated deoxygenation-reoxygenation cycles for 15 hours at 37 degrees C. Under these conditions, approximately 20 to 30 percent of the red blood cells present formed ISCs. The amount of ISCs formed in the presence of a $Ca^{+2}$ channel blocking drug under identical conditions was measured and the amount of inhibition of formation of ISCs determined.

EXAMPLE I

The amount of ISCs present in a blood sample was determined by overlaying the blood sample to be tested on a preformed density graident solution [See *Amer. J.Hematol.*, 8, 291–297 (1980)] and centrifuged at 1500 g for 20 minutes. Blood samples from a normal subject form a single band. Blood samples from sickle cell patients form two bands; the cells in the upper band consist of normal biconcave-shaped coils and the cells in the lower band consist of ISC.

A. Preparation of Density Gradient Solution

A 50 ml portion of a mixture of 53 percent (v/v) percoll, commercially available from Pharmacia, Piscataway, N.J., 18 percent (v/v) renographin-60, commercially available from Squibb, New Brunswick, NJ, 1 mM $MgCl_2$, 27 mM sodium bicarbonate, 1 mM glucose and 0.5 percent bovine serum albumin (300 mOsm/kg $H_2O$; pH 7.4) was centrifuged at 20,000 g for 15 minutes in an angle rotor (Beckman J-14) in a 15 ml. centrifuge tube to form the density gradient solution.

B. Incubation of Red Blood Cells

Whole blood was obtained from a sickle-cell patient in evacuated heparinized blood-collection tubes.

A 0.4 ml aliquot of blood was overlayed on the density gradient solution and the tube was centrifuged in a swing-rotor at 1500 g for 20 minutes. The top layer, containing normal biconcave-shaped cells, was collected and washed. The cells were washed with a suspending medium containing 110 mM NaCl, 5 mM KCl, 27 mM sodium bicarbonate, 2.4 mM sodium phosphate, 1 mM $MgCl_2$, 30 mM glucose, 1 mM adenine, 1 mM inosine and 2 percent bovine serum albumin (300 mOsm/kg $H_2O$) pH adjusted to 7.4 after equilibrating with 95 percent air/5 percent $CO_2$.

The washed cells were then suspended in the incubation medium (this suspending medium plus 2 mM $CaCl_2$) at a hematocrit value of 1 percent. Penicillin (200 units/ml) and streptomycin (0.2 mg/ml) were added to prevent the growth of bacteria during the incubation.

A 1 $\propto$ 2 ml. aliquot of the suspension containing the blood cells was pipetted into a test tube (18 mm i.d., 20 cm long), rotating at 21 rpm which had been previously flushed with a humidified gas mixture containing 95 percent air/5 percent $CO_2$, to maintain the concentration of $CO_2$ dissolved in the blood suspension. In the absence of $CO_2$ equilibrium, the $CO_2$ in the blood escapes, which increases the pH to above 8.0, damaging the red blood cells. The air/$CO_2$ atmosphere was maintained.

After 20 minutes of incubating the aliquot under the above conditions, a series of samples was prepared. The samples consisted of duplicate control samples which did not have any nitrendipine added, and a series of samples to which was added varying amounts of nitrendipine.

After another 30 minutes of incubation, the samples were subjected to a sickling process which involved the repeated deoxygenation-reoxygenation cycle. The duration of deoxygenation (95 percent air/5 percent $CO_2$) was 13 minutes and 2 minutes, respectively.

A repeated color change was observed, indicating that the cycle conditions caused deoxygenation-reoxygenation comparable to that which occurs during circulation of blood in the human body. After 15 hours of incubation, the red cell suspension was reoxygenated with 95 percent air/5 percent $CO_2$ for 30 minutes. The amount of ISCs formed in the deoxygenation-reoxygenation cycle in the presence and absence of nitrendipine was determined as follows.

A 0.5 ml aliquot of the incubated blood suspension was overlayed on top of the preformed density gradient and the tube was spun at 1500 g for 20 minutes to separate ISCs. Both the upper and lower layers were collected separately and centrifugedwashed twice in the suspending medium. The red blood cells were hemolyzed in 2 ml of 1 percent detergent (Triton X-100; commercially available from Sigma Chemical Co., St. Louis, Missouri); the pH was adjusted to 7.4 with 10 mM of a tris (hydroxymethyl) amino-methane chloride buffer and the amount of hemoglobin was determined spectrophotometrically. The percent of the amount of hemoglobin found in the lower layer, measured against the total amount of hemoglobin found in both upper and lower layers, was used as an index of the percent of ISCs in total red cells.

The test results obtained are summarized in Table I below:

TABLE I

| Nitrendipine (M) | ISC Formation (%) | ISC Inhibition (%) |
|---|---|---|
| 0 (Control) | 35.2 | 0 |
| $3 \times 10^{-9}$ | 35.2 | 0 |
| $1 \times 10^{-8}$ | 34.2 | 3 |
| $3 \times 10^{-8}$ | 26.0 | 26.1 |
| $1 \times 10^{-7}$ | 17.6 | 50.0 |

The above test results indicate that at a concentration of $1 \times 10^{-8}$M, nitrendipine inhibits the formation of ISCs to a small extent. At a concentration of $3 \times 10^{-8}$M, nitrendipine produced a 26 percent inhibition of ISC formation.

EXAMPLE II

A procedure similar to that described in Example I was carried out to determine the effect of nifedipine on the inhibition of formation of ISC.

The test results obtained are summarized in Table II below.

TABLE II

| Nifedipine (M) | ISC Formation (%) | ISC Inhibition (%) |
|---|---|---|
| 0 (Control) | 35.2 | 0 |
| $1 \times 10^{-6}$ | 31.7 | 10 |
| $1 \times 10^{-5}$ | 20.4 | 42 |
| $5 \times 10^{-5}$ | 6.3 | 82 |

The above test results indicate that at a concentration of $1 \times 10^{-6}$, nifedipine effectively inhibits the formation of ISCs.

EXAMPLE III

A procedure similar to that described in Example I was carried out to determine the effect of verapamil on the inhibition of formation of ISC.

The test results obtained are summarized in Table III below.

TABLE III

| Verapamil (M) | ISC Formation (%) | ISC Inhibition (%) |
|---|---|---|
| 0 (Control) | 35.2 | 0 |
| $1 \times 10^{-5}$ | 27.5 | 22 |
| $6 \times 10^{-5}$ | 14.8 | 58 |

The above test results indicate that at a concentration of $1 \times 10^{-5}$, verapamil effectively inhibits the formation of ISC.

What is claimed is:

1. A therapeutic method for treating sickle cell anemia in a patient having such condition which comprises administering to said patient a therapeutically effective amount of a drug capable of inhibiting the formation of irreversible sickle cells selected from the group consisting of 1,4-dihydropyridines, β-phenethylamines, benzothiazepines, ethylenediamines and diaryl alkyl amines.

2. A method as claimed in claim 1 wherein said 1,4-dihydropyridine is selected from the group consisting of nitrendipine, nifedipine, nimodipine, nisoldipine and niludipine.

3. A method as claimed in claim 1 wherein said β-phenethylamine is tiapamil or verapamil.

4. A method as claimed in claim 1 wherein said benzothiazepine is diltiazem.

5. A method as claimed in claim 1 wherein said ethylenediamine is bepridil.

6. A method as claimed in claim 1 wherein said diaryl alkyl amine is selected from the group consisting of lidoflazine, prenylamine, fendiline, terodiline, cinnarizine and flunarizine.

7. A method as claimed in claim 1 wherein said route of administration is parenteral.

8. A therapeutic method for treating sickle cell anemia in a patient having such condition which comprising administering to said patient a therapeutically effective amount of a compound capable of inhibiting the formation of irreversible sickle cells which compound is selected from the group consisting of nitrendipine, nifedipine and verapamil.

9. A therapeutic method for treating sickle cell anemia in a patient having such condition which comprises administration to said patient of from 0.1 to 100 mg/Kg of patient body weight per day of a 1,4-dihydropyridine capable of inhibiting the formation of irreversible sickle cells.

10. A method as claimed in claim 9 wherein said 1,4-dihydropyridine is nitrendipine or nifedipine.

* * * * *